Aug. 3, 1943. P. RUGGERI Plant Pat. 597
AFRICAN VIOLET
Filed June 29, 1942
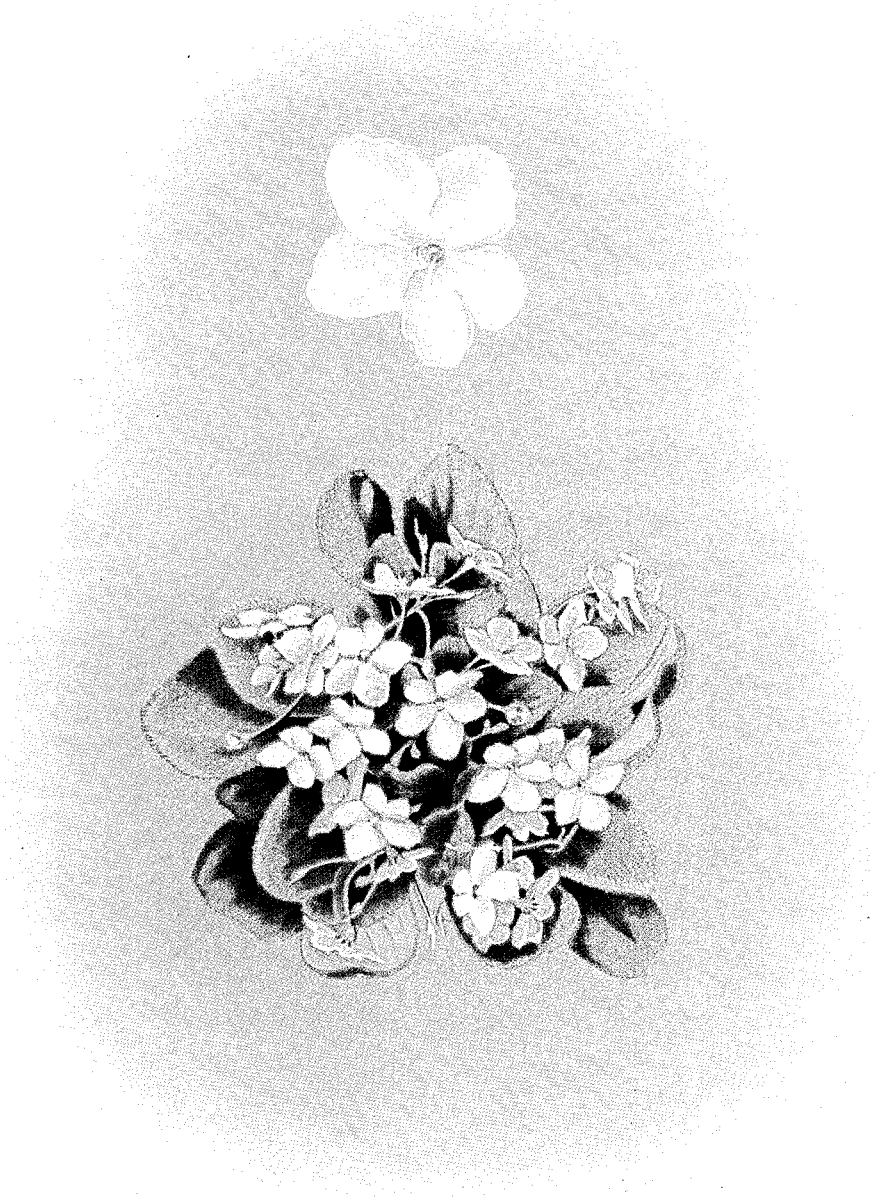
INVENTOR:
Peter Ruggeri
BY Taylor and Larragne
ATTORNEYS.

Patented Aug. 3, 1943

Plant Pat. 597

UNITED STATES PATENT OFFICE

597

AFRICAN VIOLET

Peter Ruggeri, San Francisco, Calif.

Application June 29, 1942, Serial No. 448,915

1 Claim. (Cl. 47—60)

My invention relates to a new variety of African violet plant, the novel characteristic of which resides particularly in its production of uniformly white flowers.

This new variety was originally produced by cross-pollinization of the well known blue variety of *Saintpaulia ionantha,* also known as the African violet and the Usambara violet, with a light pink spontaneously occurring sport of the same species. I first selected a specimen of this pink sport, and, as this specimen was nearing full maturity, pollen therefrom was placed on the stigma of a flower of the conventional blue variety of this species. From the seed produced by the latter, plants were grown, some of which produced the conventional blue flowers, some of which produced the previously known pink sport, and a few of which plants uniformly produced the white flowers characteristic of the variety which I regard as my invention.

This new variety uniformly producing white flowers, was reproduced asexually by rooting leaf cuttings in sand or a similar rooting medium, in the manner in which African violet plants are customarily propagated, and it has been demonstrated that all of the new variety so propagated uniformly produce the characteristic white flowers.

In structure, as distinguished from color, the flowers and foliage of my new variety bear a close similarity to the species *Saintpaulia ionantha,* the plant being gesneriaceous with nodding flowers having a calyx of five substantially erect sepals, a nearly rotate bilabiate zygomorphic corolla. The upper surfaces of the petals, however, have a distinct sheen and merge into a single structure to form the corolla tube, so that they do not fall off separately.

In color, the flowers are pure white, only a slight touch of green being visible interiorly of the corolla tube. The twin stamen heads are of approximately the Primuline Yellow color as shown on Plate XVI of Ridgway's "Color Standards and Nomenclature," 1912 edition. The upper surfaces of the leaves carry a large number of short silvery hairs and are of approximately the Elm Green color as shown on Plate XVII of the above identified publication, although lighter shades are visible in certain areas. The under sides of the leaves are heavily veined and are of approximately the Pale Fluorite Green color as shown on Plate XXXII of the above identified publication.

I claim:

A variety of African violet plant substantially as shown and described, characterized particularly by its white flower.

PETER RUGGERI.